US005530181A

United States Patent [19]
Howell

[11] Patent Number: 5,530,181
[45] Date of Patent: Jun. 25, 1996

[54] CORN INBREDS '899' AND '901' AND CORN HYBRID 'N5220'

[75] Inventor: Monroe E. Howell, Savannah, Mo.

[73] Assignee: Sandoz Ltd., Basel, Switzerland

[21] Appl. No.: 272,439

[22] Filed: Jul. 8, 1994

Related U.S. Application Data

[63] Continuation of Ser. No. 78,876, Jun. 16, 1993, abandoned.

[51] Int. Cl.$^6$ .............................. A01H 1/02; A01H 4/00; A01H 5/00; C12N 5/04

[52] U.S. Cl. .................. 800/200; 800/250; 800/DIG. 56; 435/240.4; 435/240.49; 435/240.5; 47/58; 47/ DIG. 1

[58] Field of Search ..................................... 800/200, 205, 800/250, DIG. 56; 435/240.1, 240.4, 240.47, 240.49, 240.5; 47/58.01, 58.03, DIG. 1

[56] References Cited

U.S. PATENT DOCUMENTS

| | | | |
|---|---|---|---|
| 4,812,599 | 3/1989 | Segebart | 800/200 |
| 5,157,208 | 10/1992 | Hoffbeck et al. | 800/200 |
| 5,245,125 | 9/1993 | Gogerty | 800/200 |

OTHER PUBLICATIONS

Hallauer et al. 1988. In Corn and Corn Improvement. Sprague et al., eds. Ch. 8:463–564.
Meghji et al. 1984. Crop Science. 24:545–549.
Wright. 1980. In Hybridization of Crop Plants. Fehr et al, eds. Ch. 8:161–176.
Wych. 1988. In Corn and Corn Improvement. Sprague et al. eds. Ch. 9:565–607.
Edallo et al. 1981. Maydica. XXVI:39–56.
Phillips et al. 1988. In Corn and Corn Improvement. Sprague et al., eds. Ch. 5:345–387.
Coe et al. 1988. In Corn and Corn Improvement. Third Edition. Sprague et al., eds. Ch. 3:81–137.
Allard. 1960. Principles of Plant Breeding. pp. 67–70.

*Primary Examiner*—Gary Benzion
*Assistant Examiner*—Erich E. Veitenheimer
*Attorney, Agent, or Firm*—Lynn Marcus-Wyner; Allen E. Norris

[57] ABSTRACT

This invention relates to inbred corn lines having the designation 899 and 901, seeds produced by said lines and hybrid corn seed produced by crossing said inbred corn lines

16 Claims, No Drawings

CORN INBREDS '899' AND '901' AND CORN HYBRID 'N5220'

This is a CONTINUATION of application Ser. No. 08/078,876, filed Jun. 16, 1993, now abandoned.

This invention relates to novel corn inbreds, plant parts and tissue of these inbreds, use of the inbreds to produce hybrid corn plants, hybrid corn plants obtained using at least one of said inbreds as a parent and parts and tissue of these hybrid corn plants.

The goals and methods of plant breeding particularly with respect to corn (*Zea mays*) and the use of inbreds in the breeding of hybrids e.g. in pedigree breeding are well known to those skilled in the art. Representative descriptions of techniques and underlying principles can be found for example in U.S. Pat. No. 4,654,466; U.S. Pat. No. 4,731,499; U.S. Pat. No. 5,159,134; R. W. Allard, Principles of Plant Breeding, John Wiley & Sons (1960) and N. F. Jensen, Plant Breeding Methodology, John Wiley & Sons (1988), the substantive content of which in this respect is incorporated herein by reference.

One aspect of the invention provides novel corn inbred 899. Inbred Corn Line 899 is a yellow dent corn inbred with superior characteristics and provides an excellent male and/or female parental line in crosses for producing first generation F1 corn hybrids. This inbred is best adapted over the Northern and Central regions of the United States. The inbred can be used to produce hybrids between approximately 100–115 relative maturity based on the Minnesota Relative Maturity Rating System for harvest moisture of grain. This inbred has rapid dry down characteristics which in hybrid combinations produces fast drying hybrids. Because of its excellent seed yield, good seed sizing and excellent pollen shed, 899 is well qualified for use as either a male or female parent in hybrid crosses.

The inbred has shown uniformity and stability within the limits of environmental influence for all the traits as described in the Variety Description Information. Most of the data in the Variety Description information was collected at Washington, Iowa. However, heat unit to shed and to silk data was collected at Phillips, Nebr., St. Joseph, Ill. and Washington, Iowa. The inbred has been self-pollinated and ear-rowed a sufficient number of generations with careful attention paid to uniformity of plant and ear type to ensure homozygosity and phenotypic stability. Seed of the line has been increased both by hand and in isolated fields with continued observation for uniformity. No variant traits have been observed or are expected in 899.

Inbred corn line 899, being substantially homozygous, can be reproduced by planting seeds of the line, growing the resulting corn plants under self-pollinating or sib-pollinating conditions with adequate isolation, and harvesting the resulting seed, using techniques familiar to the agricultural arts. Reproduction can alternatively take place using conventional tissue or cell culture methods.

899 may be further characterized by reference to the following objective descriptors.

(i) Type: Dent

Region Best Adapted: Northern and Central

Maturity: Northrup King Maturity Zone 6;=110–115 RM; FAO=500–550

US Heat Units=2660–2720

Heat Unit Emergence to 50% silk:1464

Heat Units=$\Sigma\{(Temp_{max}+Temp_{min})/2\}-50$ where Tmax≦86; Tmin≦50

Characteristics (ii) Plant

Plant height (to tassel tip): 221 cm
Ear height (to base of top ear): 81 cm
Length of top ear internode: 15 cm
Number of tillers: None
Number of ears per stalk: Slight two-ear tendency
Cytoplasm type: Normal (iii) Leaf:

Color: Light Green (HY)
Angle from Stalk: 30°–60°
Sheath Pubescence: Light (W22)
Marginal Waves: Few (WF 9)
Longitudinal Creases: Few (OH56A)
Width (widest point, ear node leaf): 10 cm
Length (Ear node leaf): 75 cm
Number of Leaves (mature plants): 14

(iv) Tassel

Number of lateral branches: 9
Branch Angle from central spike: 30°–40°
Peduncle Length (top leaf to basal branches) 11 cm
Pollen Shed: Heavy (KY21)
Anther Color: Purple
Glume Color: Green (v) Ear (Husked Ear Data Except When Stated Otherwise)

Length: 16 cm
Midpoint diameter: 37 mm
Weight: 80 gm
Kernel Rows: 16 Distinct Straight
Silk Color: Pink
Husk Color (fresh): Light Green
Husk Color (dry): Buff
Husk Extension (Harvest stage): Long (beyond ear tip)
Husk Leaf: short (<8 cm)
Shank Length: 9 cm
Shank (No. of internodes): 7
Position of Shank (dry husks): Pendent
Taper: Average (vi) Kernel (Dried)

Size (from ear mid-point)
Length: 10 mm
Width: 7 mm
Thick: 4 mm
Shape Grade (% rounds): 20–40%
Pericarp Color: Colorless
Aleurone Color: Homozygous white
Endosperm Color: yellow
Endosperm Type: Normal Starch
Gm Wt/100 Seeds (unsized): 18 gm

(vii) Cob

Diameter at mid-point: 22 mm
Strength: Strong
Color: white

(viii) Resistances (a) Disease
Northern Leaf Blight: susceptible
Southern Leaf Blight: susceptible
Others untested
(b) Insects
Cornborer: susceptible
Others untested

(ix) Variety most closely resembling 911

A further aspect of the invention provides novel corn inbred designated 901.

Inbred Corn Line 901 is a yellow dent corn inbred with superior characteristics and is an excellent female and/or an acceptable male parental line in crosses for producing first generation F1 corn hybrids. This inbred is best adapted over the Northern and Central regions of the United States. The inbred can be used to produce hybrids between approximately 105–115 relative maturity based on the Minnesota Relative Maturity Rating System for harvest moisture of grain. Because of its excellent seed yield, good seed sizing and acceptable pollen shed, 901 is not only well qualified for use as a female parent but can also be used as a male parent in hybrid crosses.

The inbred has shown uniformity and stability within the limits of environmental influence for all traits described in the Variety Description Information. Most of the data in the Variety Description Information was collected at Washington, Iowa. However, heat unit to shed and to silk data were collected at Phillips, Nebr., St. Joseph, Ill. and Washington, Iowa. The inbred has been self-pollinated and ear-rowed a sufficient number of generations with careful attention paid to uniformity of plant and ear type to ensure homozygosity and phenotypic stability. Seed of the line has been increased both by hand and in isolated fields with continued observation for uniformity. No variant traits have been observed or are expected in 901.

Inbred corn line 901, being substantially homozygous, can be reproduced by planting seeds of the line, growing the resulting corn plants under self-pollinating or sib-pollinating conditions with adequate isolation, and harvesting the resulting seed, using techniques familiar to the agricultural arts. Reproduction can alternatively take place using conventional tissue or cell culture methods.

901 may be further characterized by reference to the following objective descriptors.

(i) Type: Dent

Region Best Adapted: Northern and Central
Maturity: Northrup King Maturity Zone 7; 115–120 RM; FAO=550–600
US Heat Units=2720–2800
Heat Unit (HU) Emergence to 50% silk:1430

Characteristics

(ii) Plant

Plant height (to tassel tip): 217 cm
Ear height (to base of top ear): 56 cm
Length of top ear internode: 15 cm
Number of tillers: None
Number of ears per stalk: Single
Cytoplasm type: Normal

(iii) Leaf

Color: Medium Green (WF9)
Angle from Stalk: <30°
Sheath Pubescence: Heavy (OH26)
Marginal Waves: None (HY)
Longitudinal Creases: Absent (OH51)
Width (widest point, ear node leaf): 8 cm
Length (Ear node leaf): 72 cm
Number of Leaves (mature plants): 11

(iv) Tassel

Number lateral branches: 8
Branch Angle from central spike: 30–40°
Peduncle Length (top leaf to basal branches) 11 cm
Pollen Shed: Heavy (KY21)
Anther Color: Salmon
Glume Color: Green

(v) Ear (Husked Ear Data Except When Stated Otherwise)

Length: 12 cm
Midpoint diameter: 8 mm
Weight: 99 gm
Kernel Rows: 16 Distinct Straight
Silk Color: Pink
Husk Color (fresh): Light Green
Husk Color (dry): Buff
Husk Extension (Harvest stage): Medium (barely covering ear)
Husk Leaf: short (<8 cm)
Shank Length: 7 cm
Shank (No. of internodes): 7
Position of Shank (dry husks): Pendent
Taper of Ear: Average taper

(vi) Kernel (Dried)

Size (from ear mid-point)
Length: 12 mm
Width: 8 mm
Thick: 4 mm
Shape Grade (% rounds): 40–60%
Pericarp Color: Colorless
Aleurone Color: Homozygous white
Endosperm Color: yellow
Endosperm Type: Normal Starch
Gm Wt/100 Seeds (unsized): 33 gm

(vii) Cob

Diameter at mid-point: 29 mm
Strength: Strong
Color: red

(viii) Resistances (a) Disease
Northern Leaf Blight: susceptible
Southern Leaf Blight: susceptible
Others untested
(b) Insects
Cornborer: susceptible
Others untested

(ix) Variety most closely resembling

W8304

899 and 901 may be propagated conventionally, i.e. by self-pollination or sib-pollination.

The invention further relates to use of the 899 and 901 as parents to produce hybrid corn. The choice of the other parent is within the skill of the corn breeder depending particularly on the characteristics and traits desired of the resulting hybrid. Suitable parents may include other inbred lines or lines which are themselves hybrids.

899 combines best with inbred lines derived from Iowa Stiff Stalk Synthetic, e.g. B73, B14, B37 and related lines.

901 combines best with lines related to C103.

899 and 901 combine particularly well with each other.

Hybrids created using 899 and/or 901 also form an aspect of the present invention along with methods of producing them. Cross-pollination is accomplished in the usual fashion. It may be desirable to utilize a male-sterile (either cytoplasmic or nuclear) female plant to prevent self-pollination. If the female plant is not male-sterile, then either physical or chemical steps (i.e. detasseling) should be taken to ensure that self-pollination does not occur. Thus, one aspect of this invention is the process of making hybrid seed comprising the steps of crossing a first plant with a second plant, wherein one of the plants is 899 or 901, and obtaining the resultant seed. The hybrid seed so produced may be grown to produce a hybrid plant, which comprises yet another aspect of this invention.

An example of such a hybrid is that known as N5220 which has 899 and 901 as its inbred parents.

Hybrid N5220 is a 105–110 relative maturity single cross hybrid, characterized by having purple anthers.

N5220 may be distinguished from known hybrid S5340 (Northrup King Co., Golden Valley, Minn.) in that N5220 has purple anthers whereas S5340 has yellow anthers and as otherwise set forth hereinafter.

N5220 may be further characterized by the following characteristics.

| | |
|---|---|
| Type | Single cross |
| Kernel type | Dent |
| Cytoplasm type | Normal |
| Maturity | |
| Northrup King Maturity zone 5; 105–110 RM; FAO = 550–600 | |
| U.S. heat units = 2580–2650 | |
| Preflowering | |
| Length of first leaf blade | Medium |
| Anthocyanic pigment of seedling | Medium |
| Juvenile plant | |
| color | Medium green |
| form | compact |
| size | Medium |
| Flowering | |
| Number of leaves | |
| below ear | 9 |
| above ear | 7 |
| Leaf angle from stalk | 30–60 degrees |
| Leaf | |
| marginal waves | Few |
| longitudinal creases | Few |
| color | Medium green |
| Number of tillers | None |
| Plant height to tassel tip | 267 cm |
| Length of top ear internode | 18 cm |
| Second internode | |
| width | 28 cm |
| length | 9 cm |
| Anthocyanic pigment of brace roots | Weak or absent |
| Shape of tassel | Loose |
| Number of lateral tassel branches | 15 |
| Tassel branch angle | Greater than 45 degrees |
| Length of largest tassel branch | Medium |
| Anther color | Purple |
| Heat units to | |
| 50% pollen shed | 1287 |
| 50% silk | 1296 |
| Silk | |
| color | Green |
| length outside of husk | 8 cm |
| Fresh husk color | Light Green |
| Ear leaf | |
| anthocyanic pigment | Weak or none |
| pubescence | Light |
| sheath pubescence | Light or none |
| length | 81 cm |
| width | 10 cm |
| Ear height | 97 cm |
| Number of | |
| nodes | 16 |
| anthocyanic nodes | 0 |
| anthocyanic internodes | 1 |
| nodes with adventitious roots | 0 |
| Peduncle length | 9 cm |
| Central spike length | Medium |
| Glume | |
| color | Green |
| band color | Green |
| Pollen shed | Medium |
| % of plants with ear wings | 14 |
| Ear wing length | 1 cm |
| Number of ears per stalk | Single |
| Maturity | |
| Husk | |
| extension | Short |
| at maturity | Flared |
| Shank | |
| length | 13 cm |
| internode number | 7 |
| Kernel | |
| rows | Distinct |
| alignment | Slightly curved |
| row number | 16 |
| Ear weight | 205 gm |

-continued

| Kernel | |
|---|---|
| 100 weight | 160 gm |
| length | 13 mm |
| width | 8 mm |
| thickness | 4 mm |
| % round kernels | Less than 20 |
| Ear | |
| position at maturity | Pendent |
| length | 19 cm |
| diameter | 51 cm |
| taper | slight |
| Cob | |
| color | Red |
| diameter | 26 mm |
| strength | Strong |
| Kernel color | |
| pericarp | Colorless |
| aleurone segregation | Homozygous |
| aleurone | White |
| endosperm | Yellow |
| kernel crown | Light yellow |
| kernel body (sides) | Yellow |
| Endosperm type | Normal |
| % of kernels showing purple plumule tip | None |

The invention is intended to cover both inbred and hybrid plants and parts thereof. This includes plant cells either isolated and cultured or in planta, protoplasts, cell tissue and tissue culture, including that from which corn plants fertile or otherwise can be regenerated, calli and clumps, and differentiated forms of plants such as embryos, pollen, stamen, anthers, flowers, kernels, ears, cobs, leaves, stalks, roots, shoots, plantlets, silks, kernels and the like.

Methods of cell and tissue culture and regeneration are well known in the art of plant molecular biology cf for example Plant Tissue Culture Manual: Fundamentals and Application Ed. K. Lindsey, Kluwer (1991), incorporated herein by reference.

As is well known corn can be put to a wide variety of uses as forage, silage or grain. Grain can be used as livestock and poultry feed and for industrial uses (food, industry, alcoholic beverages) and of course for seed.

Feed Uses Swine, Cattle, Poultry

Food Industry

Kernels, cobs

Wet milling to produce and separate germ, hull, gluten and starch. Germ is used to produce corn oil and the germ cake for feed. Starch may be packaged for human consumption or used in food products such as sauces, gravies, puddings, baking powder. Other nonedible uses include textiles, paper, adhesives, cosmetics, explosives, corn binders, laundry purposes, agricultural formulations (also with gluten).

Corn starch may also be processed to syrups and sweeteners e.g. corn syrup, high fructose corn syrup, dextrose.

Dry milling to produce breakfast foods, brewers grits, cornmeal, hominy grits, corn flour and the like.

Fuel in the form of fuel alcohol or ethanol (e.g. as gasohol)

Seed

Alcoholic beverages

Other uses stalks for cellulose e.g. in making paper and construction elements, combustible uses, etc.

For a general discussion see periodic reviews of the US Corn Industry produced by and available from the United States Department of Agriculture (USDA), Economic Research Service, Washington, DC 20250.

The following Examples illustrate the invention without restricting its scope.

EXAMPLE 1

Development of 899

Inbred 899 was derived from the commercially available hybrid 3737 by pedigree ear-to-row breeding.

Initial self-pollination of the F1 hybrid took place in Washington, Iowa. The resulting F2 plants were self-pollinated in the winter of 1985 in Waimea, Hawaii to produce F2S1 families. A selected plant of one F2S1 family was self-pollinated followed by a further 5 generations of self-pollination to produce inbred 899.

Inbred 899 is uniform and stable and appears to be homozygous for all agronomic characteristics.

EXAMPLE 2

Development of 901

901 was derived from crossing inbreds LH119 (Holdens Foundation Seed Co.) and 790 in winter 1984 and back-crossing to 790 followed by simple pedigree ear-to-row breeding for seven generations after the initial backcross.

Inbred 901 is uniform and stable and appears to be homozygous for all agronomic characteristics.

EXAMPLE 3

Development of Hybrid N5220

The cross 901×899 is made.

EXAMPLE 4

Comparative Data

N5220 may be compared to S5340 which is a commercially available hybrid. In the table below, Mst stands for percent moisture at harvest; HU Silk stands for number of heat units form plant to 50% silk.

| Hybrid | Yield Bu/A | Mst | Lodging Stalk % | Root | Dropped Ears | HU Silk |
|---|---|---|---|---|---|---|
| 1992 Replicated Yield Trial Data: 100–110 RM Markets | | | | | | |
| N5220 | 165 | 24.4 | 4 | 4 | 11 | 1291 |
| S5340 | 159 | 26.8 | 6 | 2 | 41 | 1304 |
| LSD | 7 | 0.8 | 3 | 2 | 1 | 21 |
| No. of Loc. | 34 | 34 | 32 | 28 | 31 | 6 |
| 1992 Replicated Yield Trial Data: 105–115 RM Markets | | | | | | |
| NH5220 | 170 | 20.6 | 4 | 5 | 1 | 1296 |
| S5340 | 165 | 22.0 | 5 | 5 | 12 | 1290 |
| LSD | 6 | 0.5 | 2 | 3 | 0 | 16 |
| No. of Loc. | 48 | 48 | 42 | 33 | 35 | 12 |

A deposit of at least 2500 seeds of each inbred 899, 901 and hybrid N5220 has been made available to the public without restriction with the American Type Culture Collection (ATCC) Rockville, Md. 20852 U.S.A. on December 5, 1995 as ATCC deposit no. 97362 for inbred 899; ATCC deposit no. 97363 for inbred 901 and ATCC deposit no. 97364 for hybrid N5220. The seeds deposited with the ATCC are taken from stock maintained by Northrup King Co. since prior to the filing date of this application or any parents thereof. The deposit of each line will be maintained without restriction in the ATCC depository, which is a public depository, for a period of 30 years, or 5 years after the most recent request, or for the effective life of the patent, whichever is longer, and will be replaced if it becomes nonviable during that period.

What is claimed is:

1. Inbred corn seed designated 899 having ATCC deposit no. 97362.
2. A corn plant produced by growing the seed of claim 1.
3. An inbred corn plant having all the physiological and morphological characteristics of the corn plant of claim 2.
4. Pollen of the plant of claim 2.
5. An ovule of the plant of claim 2.
6. A first generation hybrid corn plant produced by growing hybrid corn seed, wherein said seed is produced by crossing a first inbred parent corn plant with a second inbred parent corn plant wherein said first or second inbred corn plant is the corn plant of claim 2 and harvesting the resultant hybrid corn seed.
7. A corn plant regenerated from the tissue culture of tissue obtained from the corn plant of claim 2 said regenerated corn plant having all of the physiological and morphological characteristics of the corn plant of claim 2.
8. Inbred corn seed designated 901 having ATCC deposit no. 97363.
9. A corn plant produced by growing the seed of claim 8.
10. An inbred corn plant having all the physiological and morphological characteristics of the corn plant of claim 9.
11. Pollen of the plant of claim 9.
12. An ovule of the plant of claim 9.
13. A first generation hybrid corn plant produced by growing hybrid corn seed, wherein said seed is produced by crossing a first inbred parent corn plant with a second inbred parent corn plant wherein said first or second inbred corn plant is the corn plant of claim 9 and harvesting the resultant hybrid corn seed.
14. A corn plant regenerated from the tissue culture of tissue obtained from the corn plant of claim 9 said regenerated corn plant having all of the physiological and morphological characteristics of the corn plant of claim 9.
15. A F1 hybrid corn plant designated N5220 produced by growing hybrid corn seed, wherein said hybrid seed is produced by crossing a first inbred corn plant with a second inbred corn plant and harvesting the hybrid seed and wherein said first inbred corn plant is produced by growing the seed designated 899 having ATCC deposit no. 97362 and second inbred corn plant is produced by growing the seed designated 901 having ATCC deposit no. 97363.
16. Seeds produced by the cultivation of the F1 hybrid corn plant of claim 15.

* * * * *